United States Patent
Keret et al.

(10) Patent No.: US 12,419,692 B2
(45) Date of Patent: Sep. 23, 2025

(54) ROBOTIC ARM NAVIGATION USING VIRTUAL BONE MOUNT

(71) Applicant: Mazor Robotics Ltd., Caesarea (IL)

(72) Inventors: Amir Keret, Atlit (IL); Ziv Seemann, Beit Ytzhack (IL); Ori Ben Zeev, Ramat HaSharon (IL); Adi Sandelson, Givatayim (IL); Gal Barazani, Tirat Carmel (IL); Nimrod Dori, Atlit (IL)

(73) Assignee: Mazor Robotics Ltd., Caesarea (IL)

( * ) Notice: Subject to any disclaimer, the term of this patent is extended or adjusted under 35 U.S.C. 154(b) by 721 days.

(21) Appl. No.: 17/735,878

(22) Filed: May 3, 2022

(65) Prior Publication Data

US 2023/0355314 A1    Nov. 9, 2023

(51) Int. Cl.
*A61B 34/20* (2016.01)
*A61B 34/00* (2016.01)
*A61B 34/30* (2016.01)

(52) U.S. Cl.
CPC ............. *A61B 34/20* (2016.02); *A61B 34/30* (2016.02); *A61B 2034/2055* (2016.02); *A61B 2034/2057* (2016.02); *A61B 34/25* (2016.02)

(58) Field of Classification Search
CPC ......... A61B 34/20; A61B 34/30; A61B 34/25; A61B 2034/2055; A61B 2034/2057; A61B 90/96; A61B 2090/3966; A61B 2090/3983; A61B 2090/3995; A61B 90/39
See application file for complete search history.

(56) References Cited

U.S. PATENT DOCUMENTS

| | | |
|---|---|---|
| 4,870,592 A | 9/1989 | Lampi et al. |
| 5,343,391 A | 8/1994 | Mushabac |
| 6,033,415 A | 3/2000 | Mittelstadt et al. |
| 6,322,567 B1 | 11/2001 | Mittelstadt et al. |
| 6,430,434 B1 | 8/2002 | Mittelstadt |
| 6,788,018 B1 | 9/2004 | Blumenkranz |
| 8,104,958 B2 | 1/2012 | Weiser et al. |
| 8,400,094 B2 | 3/2013 | Schena |

(Continued)

FOREIGN PATENT DOCUMENTS

| | | |
|---|---|---|
| DE | 202005014582 | 2/2007 |
| KR | 10-2017-0091588 | 8/2017 |

(Continued)

OTHER PUBLICATIONS

International Search Report and Written Opinion for International (PCT) Patent Application No. PCT/IL2023/050436, dated Aug. 25, 2023, 16 pages.

*Primary Examiner* — Sohana Tanju Khayer
(74) *Attorney, Agent, or Firm* — Sheridan Ross P.C.

(57) ABSTRACT

A system according to at least one embodiment of the present disclosure includes a processor; and a memory storing data thereon that, when processed by the processor, cause the processor to: determine, based on a navigation element of a first type and a navigation element of a second type both disposed on a navigation tracker, a first registration between the navigation tracker and an anatomical element; determine, based on a navigation element of a third type disposed on the navigation tracker, a second registration between a robotic arm and the navigation tracker; and navigate, based on the first registration and the second registration, the robotic arm relative to the anatomical element.

20 Claims, 6 Drawing Sheets

(56) References Cited

U.S. PATENT DOCUMENTS

| | | |
|---|---|---|
| 10,391,635 B2 | 8/2019 | Berghofer et al. |
| 10,842,461 B2 | 11/2020 | Johnson et al. |
| 2005/0234327 A1 | 10/2005 | Saracen et al. |
| 2009/0080737 A1 | 3/2009 | Battle et al. |
| 2009/0314925 A1 | 12/2009 | Van Vorhis et al. |
| 2012/0085934 A1 | 4/2012 | Marcelis et al. |
| 2013/0060146 A1* | 3/2013 | Yang ............... A61B 34/20 600/476 |
| 2015/0335480 A1 | 11/2015 | Alvarez et al. |
| 2018/0185100 A1 | 7/2018 | Weinstein et al. |
| 2019/0038268 A1 | 2/2019 | Kopp |
| 2019/0090800 A1 | 3/2019 | Bosworth et al. |
| 2019/0090955 A1* | 3/2019 | Singh ............... A61B 17/00 |
| 2019/0206565 A1 | 7/2019 | Shelton, IV |
| 2020/0069376 A1 | 3/2020 | Garcia et al. |
| 2020/0078097 A1* | 3/2020 | Gregerson ........ B25J 9/1666 |
| 2020/0129241 A1 | 4/2020 | Forstein et al. |
| 2020/0188032 A1 | 6/2020 | Komp et al. |
| 2020/0222127 A1* | 7/2020 | Snyder ............. A61B 90/37 |
| 2020/0229879 A1* | 7/2020 | Magaraggia ...... A61B 34/30 |
| 2020/0281742 A1 | 9/2020 | Wu et al. |
| 2020/0297228 A1 | 9/2020 | Crawford et al. |
| 2020/0315737 A1 | 10/2020 | Crawford et al. |
| 2020/0337780 A1 | 10/2020 | Winkler et al. |
| 2020/0384287 A1 | 12/2020 | Hetz |
| 2021/0030479 A1* | 2/2021 | Marti ............... A61B 34/20 |
| 2021/0145523 A1 | 5/2021 | Xing et al. |
| 2021/0169582 A1 | 6/2021 | Li et al. |
| 2021/0267609 A1 | 9/2021 | Nguyen et al. |
| 2021/0275260 A1 | 9/2021 | Kang et al. |
| 2021/0322032 A1 | 10/2021 | Gogarty et al. |
| 2023/0390021 A1* | 12/2023 | Polchin ............. G06T 7/337 |

FOREIGN PATENT DOCUMENTS

| | | |
|---|---|---|
| WO | WO 2004/096502 | 11/2004 |
| WO | WO 2004/100812 | 11/2004 |
| WO | WO 2008/094766 | 8/2008 |
| WO | WO 2010/068005 | 6/2010 |
| WO | WO 2010/068213 | 6/2010 |
| WO | WO 2015/087335 | 6/2015 |
| WO | WO 2017/122202 | 7/2017 |
| WO | WO 2018/053282 | 3/2018 |
| WO | WO 2020/181076 | 9/2020 |
| WO | WO 2020/185930 | 9/2020 |
| WO | WO 2021/011280 | 1/2021 |
| WO | WO 2021/062001 | 4/2021 |
| WO | WO 2021/219502 | 11/2021 |

* cited by examiner

ROBOTIC ARM NAVIGATION USING VIRTUAL BONE MOUNT

BACKGROUND

The present disclosure is generally directed to surgical navigation, and relates more particularly to surgical navigation using navigation trackers.

Surgical robots may assist a surgeon or other medical provider in carrying out a surgical procedure, or may complete one or more surgical procedures autonomously. Imaging may be used by a medical provider for diagnostic and/or therapeutic purposes. Patient anatomy can change over time, particularly following placement of a medical implant in the patient anatomy.

BRIEF SUMMARY

Example aspects of the present disclosure include:

A system according to at least one embodiment of the present disclosure comprises: a processor; and a memory storing data thereon that, when processed by the processor, cause the processor to: determine, based on a navigation element of a first type and a navigation element of a second type both disposed on a navigation tracker, a first registration between the navigation tracker and an anatomical element; determine, based on a navigation element of a third type disposed on the navigation tracker, a second registration between a robotic arm and the navigation tracker; and navigate, based on the first registration and the second registration, the robotic arm relative to the anatomical element.

Any of the aspects herein, wherein the navigation element of the first type, the navigation element of the second type, and the navigation element of the third type are disposed on the navigation tracker in a predetermined configuration.

Any of the aspects herein, wherein the navigation element of the third type comprises a first optical tracking marker tracked by a third imaging device, and wherein determining the second registration comprises the processor: receiving, from the third imaging device, information about a first location of the first optical tracking marker and a first pose of the robotic arm; and determining, based on the information about the first location of the first optical tracking marker and the first pose of the robotic arm, a position of the robotic arm relative to the first optical tracking marker.

Any of the aspects herein, wherein the navigation element of the first type includes a plurality of fluoroscopic markers capable of being detected by a first imaging device, and wherein determining the first registration comprises the processor: receiving, from the first imaging device, a plurality of images depicting the plurality of fluoroscopic markers and the anatomical element; and determining, based on the plurality of images, a position of each fluoroscopic marker of the plurality of fluoroscopic markers relative to the anatomical element.

Any of the aspects herein, wherein the navigation element of the second type includes a plurality of navigation markers capable of being detected by a second imaging device, and wherein determining the first registration further comprises the processor: receiving, from the second imaging device, information about a position of each navigation marker of the plurality of navigation markers; and determining, based on the information about the position of each navigation marker and the predetermined configuration, a position of each navigation marker relative to the anatomical element.

Any of the aspects herein, wherein the robotic arm includes a second optical tracking marker, and wherein the third imaging device tracks the second optical tracking marker.

Any of the aspects herein, wherein the first imaging device comprises a fluoroscopic imaging device, wherein the second imaging device comprises a navigation camera, and wherein the third imaging device comprises a laser tracker.

Any of the aspects herein, wherein the navigation tracker is disposed on a patient table, wherein the robotic arm is disposed on a second table a first distance from the patient table, and wherein the third imaging device is disposed a second distance from the robotic arm.

Any of the aspects herein, wherein the first imaging device comprises an O-arm, wherein the second imaging device comprises a navigation camera, and wherein the third imaging device comprises a three-dimensional (3D) camera.

A system according to at least one embodiment of the present disclosure comprises: a robotic arm disposed a first distance from a patient bed; a processor; and a memory storing data thereon that, when processed by the processor, cause the processor to: determine, based on a navigation element of a first type and a navigation element of a second type both disposed on a navigation tracker, a first registration between the navigation tracker and an anatomical element; determine, based on a navigation element of a third type disposed on the navigation tracker, a second registration between the robotic arm and the navigation tracker; and determine, based on the first registration and the second registration, a first pose of the robotic arm relative to the anatomical element.

Any of the aspects herein, wherein the navigation element of the first type, the navigation element of the second type, and the navigation element of the third type are disposed on the navigation tracker in a predetermined configuration.

Any of the aspects herein, wherein the navigation element of the third type comprises an optical tracking target tracked by a third imaging device, and wherein determining the second registration comprises the processor: receiving, from the third imaging device, first information about a first pose of the optical tracking target; and determining, based on the first information about the first pose of the optical tracking target and the predetermined configuration, a first position of the robotic arm relative to the navigation tracker.

Any of the aspects herein, wherein the navigation element of the first type includes a plurality of fluoroscopic markers capable of being detected by a fluoroscopic imaging device, and wherein the first registration comprises the processor: receiving, from the fluoroscopic imaging device, a plurality of images depicting the plurality of fluoroscopic markers and the anatomical element; and determining, based on the plurality of images, a position of each fluoroscopic marker of the plurality of fluoroscopic markers relative to the anatomical element.

Any of the aspects herein, wherein the navigation element of the second type includes a plurality of navigation markers capable of being detected by a second imaging device, and wherein the first registration further comprises the processor: receiving, from the second imaging device, information about a position of each navigation marker of the plurality of navigation markers; and determining, based on the information about the position of each navigation marker and the predetermined configuration, a position of each navigation marker relative to the anatomical element.

Any of the aspects herein, wherein the third imaging device is disposed proximate an end effector of the robotic arm.

Any of the aspects herein, wherein the robotic arm is disposed on a second table, the second table capable of moving relative to the patient bed.

Any of the aspects herein, wherein the second imaging device comprises a navigation camera, and wherein the third imaging device comprises a laser tracker.

A method according to at least one embodiment of the present disclosure comprises: determining, based on a first plurality of images captured by a first imaging device, a first registration between a plurality of fluoroscopic markers disposed on a navigation tracker and an anatomical element; determining, based on a second plurality of image captured by a second imaging device, a second registration between a plurality of navigation markers disposed on the navigation tracker and the anatomical element; determining, based on an optical sensor tracker target disposed on the navigation tracker, a third registration between the navigation tracker and a robotic arm; and moving, based on the second registration and the third registration, the robotic arm relative to the anatomical element.

Any of the aspects herein, wherein the plurality of fluoroscopic markers, the plurality of navigation markers, and the optical sensor tracker target are disposed in a fixed orientation on the navigation tracker.

Any of the aspects herein, wherein the optical sensor tracker target is tracked by a third imaging device, and wherein the determining the third registration further comprises: receiving, from the third imaging device, information describing a first location of the optical sensor tracker target relative to the robotic arm; and determining, based on the information describing the first location of the optical sensor tracker target, a first pose of the robotic arm relative to the navigation tracker.

Any aspect in combination with any one or more other aspects.

Any one or more of the features disclosed herein.

Any one or more of the features as substantially disclosed herein.

Any one or more of the features as substantially disclosed herein in combination with any one or more other features as substantially disclosed herein.

Any one of the aspects/features/embodiments in combination with any one or more other aspects/features/embodiments.

Use of any one or more of the aspects or features as disclosed herein.

It is to be appreciated that any feature described herein can be claimed in combination with any other feature(s) as described herein, regardless of whether the features come from the same described embodiment.

The details of one or more aspects of the disclosure are set forth in the accompanying drawings and the description below. Other features, objects, and advantages of the techniques described in this disclosure will be apparent from the description and drawings, and from the claims.

The phrases "at least one", "one or more", and "and/or" are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together. When each one of A, B, and C in the above expressions refers to an element, such as X, Y, and Z, or class of elements, such as X1-Xn, Y1-Ym, and Z1-Zo, the phrase is intended to refer to a single element selected from X, Y, and Z, a combination of elements selected from the same class (e.g., X1 and X2) as well as a combination of elements selected from two or more classes (e.g., Y1 and Zo).

The term "a" or "an" entity refers to one or more of that entity. As such, the terms "a" (or "an"), "one or more" and "at least one" can be used interchangeably herein. It is also to be noted that the terms "comprising", "including", and "having" can be used interchangeably.

The preceding is a simplified summary of the disclosure to provide an understanding of some aspects of the disclosure. This summary is neither an extensive nor exhaustive overview of the disclosure and its various aspects, embodiments, and configurations. It is intended neither to identify key or critical elements of the disclosure nor to delineate the scope of the disclosure but to present selected concepts of the disclosure in a simplified form as an introduction to the more detailed description presented below. As will be appreciated, other aspects, embodiments, and configurations of the disclosure are possible utilizing, alone or in combination, one or more of the features set forth above or described in detail below.

Numerous additional features and advantages of the present disclosure will become apparent to those skilled in the art upon consideration of the embodiment descriptions provided hereinbelow.

BRIEF DESCRIPTION OF THE SEVERAL VIEWS OF THE DRAWINGS

The accompanying drawings are incorporated into and form a part of the specification to illustrate several examples of the present disclosure. These drawings, together with the description, explain the principles of the disclosure. The drawings simply illustrate preferred and alternative examples of how the disclosure can be made and used and are not to be construed as limiting the disclosure to only the illustrated and described examples. Further features and advantages will become apparent from the following, more detailed, description of the various aspects, embodiments, and configurations of the disclosure, as illustrated by the drawings referenced below.

DETAILED DESCRIPTION

Figure 1:
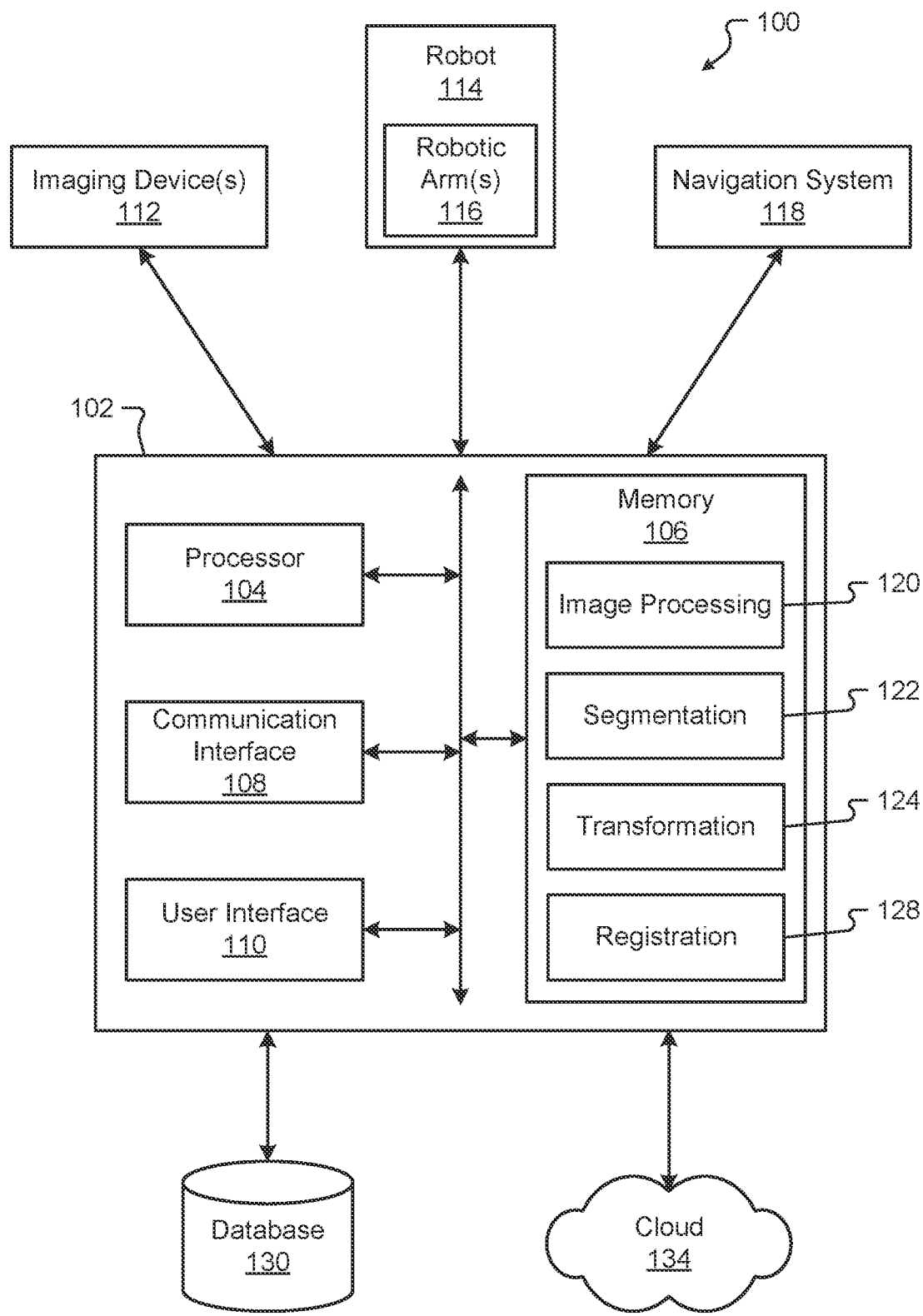
FIG. 1 is a block diagram of a system according to at least one embodiment of the present disclosure.

It should be understood that various aspects disclosed herein may be combined in different combinations than the combinations specifically presented in the description and accompanying drawings. It should also be understood that, depending on the example or embodiment, certain acts or events of any of the processes or methods described herein may be performed in a different sequence, and/or may be added, merged, or left out altogether (e.g., all described acts or events may not be necessary to carry out the disclosed techniques according to different embodiments of the present disclosure). In addition, while certain aspects of this disclosure are described as being performed by a single module or unit for purposes of clarity, it should be understood that the techniques of this disclosure may be performed by a combination of units or modules associated with, for example, a computing device and/or a medical device.

In one or more examples, the described methods, processes, and techniques may be implemented in hardware, software, firmware, or any combination thereof. If implemented in software, the functions may be stored as one or more instructions or code on a computer-readable medium and executed by a hardware-based processing unit. Alternatively or additionally, functions may be implemented using machine learning models, neural networks, artificial neural networks, or combinations thereof (alone or in combination with instructions). Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors (e.g., Intel Core i3, i5, i7, or i9 processors; Intel Celeron processors; Intel Xeon processors; Intel Pentium processors; AMD Ryzen processors; AMD Athlon processors; AMD Phenom processors; Apple A10 or 10× Fusion processors; Apple A11, A12, A12X, A12Z, or A13 Bionic processors; or any other general purpose microprocessors), graphics processing units (e.g., Nvidia GeForce RTX 2000-series processors, Nvidia GeForce RTX 3000-series processors, AMD Radeon RX 5000-series processors, AMD Radeon RX 6000-series processors, or any other graphics processing units), application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

Before any embodiments of the disclosure are explained in detail, it is to be understood that the disclosure is not limited in its application to the details of construction and the arrangement of components set forth in the following description or illustrated in the drawings. The disclosure is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Further, the present disclosure may use examples to illustrate one or more aspects thereof. Unless explicitly stated otherwise, the use or listing of one or more examples (which may be denoted by "for example," "by way of example," "e.g.," "such as," or similar language) is not intended to and does not limit the scope of the present disclosure.

The terms proximal and distal are used in this disclosure with their conventional medical meanings, proximal being closer to the operator or user of the system, and further from the region of surgical interest in or on the patient, and distal being closer to the region of surgical interest in or on the patient, and further from the operator or user of the system.

A floor mounted robot may be navigated to patient anatomy during a surgery or surgical procedure. The floor mounted robot, however, cannot be fixed rigidly to the patient anatomy because the robotic arm may create unwanted forces on the patient anatomy. Alternatively, the floor mounted robot may be mounted to the patient bed, resulting in increased accuracy, but mounting the robot to the bed may restrict the movement of the robotic arm, and the bed may be subject to weight limitations that may be exceeded by adding the robot to the bed.

In at least one embodiment of the present disclosure, a navigation tracker is provided that enables a navigation system, for example using a Network Digital Interface (NDI) camera, to track navigation markers disposed on the navigation tracker. The navigation tracker may also include fluoroscopy markers, which may enable the use of fluoro-registration of the robotic space to the anatomy. The navigation tracker may also include a high accuracy optical tracker to permit the location in space of the robot relative to the navigation tracker to be tracked. In other words, the navigation tracker may act as a virtual bone mount, enabling the robot to be virtually mounted to the patient anatomy. The robot may include a tracking system to track the patient anatomy, and the tracking system may be calibrated to the robot location. In some embodiments, an end effector of the robot may include a tracking marker that can be tracked by the tracking system. In such embodiments, the tracking system may be positioned in another area of the surgical environment and may track both the robot and the navigation tracker. The use of the virtual bone mount may enable the use of a floor-mounted robot without compromising on accuracy gained when mounting the robot to patient anatomy.

The navigation tracker may act as a patient tracker by including navigation markers that enable a navigation system to move instruments relative to the patient, metal markers to permit Computed Tomography-Fluoroscopy registration, and an optical sensor base to enable a floor-mounted robot to determine its position relative to patient anatomy.

In some embodiments, the optical sensor may include a 3D camera target. The 3D camera target may include a plurality of faces capable of being detected by a three-dimensional (3D) camera. The 3D camera may focus on the target and/or another 3D camera target on the robotic arm, and track the movements thereof. The use of the 3D camera targets may enable on-the-fly tracking of the navigation tracker relative to the robot, and vice versa. The use of the 3D camera targets may also enhance the fluoroscopic images captured when registering the tracker to the patient anatomy, since the 3D camera target may not appear in the fluoroscopic images. In some embodiments, alternative 3D cameras may be used (e.g., a ClaroNav® navigation camera).

In some embodiments, the optical sensor may include a laser target. A laser tracker may generate and propagate a laser onto the laser target. The laser target may reflect the laser back to laser tracker, enabling the laser tracker to determine the position and/or orientation of the laser target. In some embodiments, the laser tracker may have two, three, four, five, or six or more degrees of freedom.

In some embodiments, the patient may be placed on a surgical bed and additional preparations (e.g., surgical planning) may be made. The robot may be draped in or near the operating room or other surgical environment. Two or more fluoroscopic images depicting the patient and the navigation tracker may be taken, and one or more machine learning or artificial intelligence models may determine, based on the fluoroscopic images, a registration between the navigation tracker and the patient anatomy. Additionally, a navigation system may detect the navigation tracker based on the navigation markers disposed thereon, and may use the identification of the navigation markers along with the registration to navigate, for example, the robot. The robot may then be moved proximate to the patient table, and the measurement or optical sensor may be aimed at the measurement or optical tracker disposed on the navigation tracker. The alignment of the sensor and the tracker may enable the navigation system to determine the position of the robot relative to the patient anatomy.

In some embodiments, an O-arm may be used to register the patient with the navigation tracker and the navigation camera. The navigation system may similarly use the navigation markers on the navigation tracker and the registration of the O-arm to navigate the robot. The robot may then be aligned near the bed, and the measurement or optical sensor may be aimed at the measurement or optical tracker to enable the navigation system to know where the navigation tracker is relative to the robot (based on the measurement or optical sensor) as well as where the navigation tracker is relative to the anatomy (based on the navigation markers and the registration). This may enable the navigation system to control the robot relative to the patient anatomy.

Embodiments of the present disclosure provide technical solutions to one or more of the problems of (1) inaccurate tracking of a robotic arm relative to patient anatomy when the robotic arm is not mounted to the patient bed, and (2) limitations/restrictions on robotic arm movement when the robotic arm is mounted to a patient bed.

Turning first to FIG. 1, a block diagram of a system 100 according to at least one embodiment of the present disclosure is shown. The system 100 may be used to navigate a robotic arm relative to patient anatomy, determine one or more registrations of patient anatomy to a navigation tracker and/or a robotic arm, and/or to carry out one or more other aspects of one or more of the methods discussed herein. The system 100 comprises a computing device 102, one or more imaging devices 112, a robot 114, a navigation system 118, a database 130, and/or a cloud or other network 134. Systems according to other embodiments of the present disclosure may comprise more or fewer components than the system 100. For example, the system 100 may not include the imaging device 112, the robot 114, the navigation system 118, one or more components of the computing device 102, the database 130, and/or the cloud 134.

The computing device 102 comprises a processor 104, a memory 106, a communication interface 108, and a user interface 110. Computing devices according to other embodiments of the present disclosure may comprise more or fewer components than the computing device 102.

The processor 104 of the computing device 102 may be any processor described herein or any similar processor. The processor 104 may be configured to execute instructions stored in the memory 106, which instructions may cause the processor 104 to carry out one or more computing steps utilizing or based on data received from the imaging device 112, the robot 114, the navigation system 118, the database 130, and/or the cloud 134.

The memory 106 may be or comprise RAM, DRAM, SDRAM, other solid-state memory, any memory described herein, or any other tangible, non-transitory memory for storing computer-readable data and/or instructions. The memory 106 may store information or data useful for completing, for example, any step of the methods 400 and/or 500 described herein, or of any other methods. The memory 106 may store, for example, instructions and/or machine learning models that support one or more functions of the robot 114. For instance, the memory 106 may store content (e.g., instructions and/or machine learning models) that, when executed by the processor 104, enable image processing 120, segmentation 122, transformation 124, and/or registration 128. Such content, if provided as in instruction, may, in some embodiments, be organized into one or more applications, modules, packages, layers, or engines. Alternatively or additionally, the memory 106 may store other types of content or data (e.g., machine learning models, artificial neural networks, deep neural networks, etc.) that can be processed by the processor 104 to carry out the various method and features described herein. Thus, although various contents of memory 106 may be described as instructions, it should be appreciated that functionality described herein can be achieved through use of instructions, algorithms, and/or machine learning models. The data, algorithms, and/or instructions may cause the processor 104 to manipulate data stored in the memory 106 and/or received from or via the imaging device 112, the robot 114, the database 130, and/or the cloud 134.

The computing device 102 may also comprise a communication interface 108. The communication interface 108 may be used for receiving image data or other information from an external source (such as the imaging device 112, the robot 114, the navigation system 118, the database 130, the cloud 134, and/or any other system or component not part of the system 100), and/or for transmitting instructions, images, or other information to an external system or device (e.g., another computing device 102, the imaging device 112, the robot 114, the navigation system 118, the database 130, the cloud 134, and/or any other system or component not part of the system 100). The communication interface 108 may comprise one or more wired interfaces (e.g., a USB port, an Ethernet port, a Firewire port) and/or one or more wireless transceivers or interfaces (configured, for example, to transmit and/or receive information via one or more wireless communication protocols such as 802.11a/b/g/n, Bluetooth, NFC, ZigBee, and so forth). In some embodiments, the communication interface 108 may be useful for enabling the device 102 to communicate with one or more other processors 104 or computing devices 102, whether to reduce the time needed to accomplish a computing-intensive task or for any other reason.

The computing device 102 may also comprise one or more user interfaces 110. The user interface 110 may be or comprise a keyboard, mouse, trackball, monitor, television, screen, touchscreen, and/or any other device for receiving information from a user and/or for providing information to a user. The user interface 110 may be used, for example, to receive a user selection or other user input regarding any step of any method described herein. Notwithstanding the foregoing, any required input for any step of any method described herein may be generated automatically by the system 100 (e.g., by the processor 104 or another component of the system 100) or received by the system 100 from a source external to the system 100. In some embodiments, the user interface 110 may be useful to allow a surgeon or other user to modify instructions to be executed by the processor 104 according to one or more embodiments of the present disclosure, and/or to modify or adjust a setting of other information displayed on the user interface 110 or corresponding thereto.

Although the user interface 110 is shown as part of the computing device 102, in some embodiments, the computing device 102 may utilize a user interface 110 that is housed separately from one or more remaining components of the computing device 102. In some embodiments, the user interface 110 may be located proximate one or more other components of the computing device 102, while in other embodiments, the user interface 110 may be located remotely from one or more other components of the computing device 102.

The imaging device 112 may be operable to image anatomical feature(s) (e.g., a bone, veins, tissue, etc.) and/or other aspects of patient anatomy to yield image data (e.g., image data depicting or corresponding to a bone, veins, tissue, etc.). "Image data" as used herein refers to the data generated or captured by an imaging device 112, including in a machine-readable form, a graphical/visual form, and in any other form. In various examples, the image data may comprise data corresponding to an anatomical feature of a patient, or to a portion thereof. The image data may be or comprise a preoperative image, an intraoperative image, a postoperative image, or an image taken independently of any surgical procedure. In some embodiments, a first imaging device 112 may be used to obtain first image data (e.g., a first image) at a first time, and a second imaging device 112 may be used to obtain second image data (e.g., a second image) at a second time after the first time. The imaging device 112 may be capable of taking a 2D image or a 3D image to yield the image data. The imaging device 112 may be or comprise, for example, an ultrasound scanner (which may comprise, for example, a physically separate transducer and receiver, or a single ultrasound transceiver), an O-arm, a C-arm, a G-arm, or any other device utilizing X-ray-based imaging (e.g., a fluoroscope, a CT scanner, or other X-ray machine), a magnetic resonance imaging (MRI) scanner, an optical coherence tomography (OCT) scanner, an endoscope, a microscope, an optical camera, a thermographic camera (e.g., an infrared camera), a radar system (which may comprise, for example, a transmitter, a receiver, a processor, and one or more antennae), or any other imaging device 112 suitable for obtaining images of an anatomical feature of a patient. The imaging device 112 may be contained entirely within a single housing, or may comprise a transmitter/emitter and a receiver/detector that are in separate housings or are otherwise physically separated.

In some embodiments, the imaging device 112 may comprise more than one imaging device 112. For example, a first imaging device may provide first image data and/or a first image, and a second imaging device may provide second image data and/or a second image. In still other embodiments, the same imaging device may be used to provide both the first image data and the second image data, and/or any other image data described herein. The imaging device 112 may be operable to generate a stream of image data. For example, the imaging device 112 may be configured to operate with an open shutter, or with a shutter that continuously alternates between open and shut so as to capture successive images. For purposes of the present disclosure, unless specified otherwise, image data may be considered to be continuous and/or provided as an image data stream if the image data represents two or more frames per second.

The robot 114 may be any surgical robot or surgical robotic system. The robot 114 may be or comprise, for example, the Mazor X™ Stealth Edition robotic guidance system. The robot 114 may be configured to position the imaging device 112 at one or more precise position(s) and orientation(s), and/or to return the imaging device 112 to the same position(s) and orientation(s) at a later point in time. The robot 114 may additionally or alternatively be configured to manipulate a surgical tool (whether based on guidance from the navigation system 118 or not) to accomplish or to assist with a surgical task. In some embodiments, the robot 114 may be configured to hold and/or manipulate an anatomical element during or in connection with a surgical procedure. The robot 114 may comprise one or more robotic arms 116. In some embodiments, the robotic arm 116 may comprise a first robotic arm and a second robotic arm, though the robot 114 may comprise more than two robotic arms. In some embodiments, one or more of the robotic arms 116 may be used to hold and/or maneuver the imaging device 112. In embodiments where the imaging device 112 comprises two or more physically separate components (e.g., a transmitter and receiver), one robotic arm 116 may hold one such component, and another robotic arm 116 may hold another such component. Each robotic arm 116 may be positionable independently of the other robotic arm. The robotic arms 116 may be controlled in a single, shared coordinate space, or in separate coordinate spaces.

The robot 114, together with the robotic arm 116, may have, for example, one, two, three, four, five, six, seven, or more degrees of freedom. Further, the robotic arm 116 may be positioned or positionable in any pose, plane, and/or focal point. The pose includes a position and an orientation. As a result, an imaging device 112, surgical tool, or other object held by the robot 114 (or, more specifically, by the robotic arm 116) may be precisely positionable in one or more needed and specific positions and orientations.

The robotic arm(s) 116 may comprise one or more sensors that enable the processor 104 (or a processor of the robot 114) to determine a precise pose in space of the robotic arm (as well as any object or element held by or secured to the robotic arm).

In some embodiments, reference markers (e.g., navigation markers) may be placed on the robot 114 (including, e.g., on the robotic arm 116), the imaging device 112, or any other object in the surgical space. The reference markers may be tracked by the navigation system 118, and the results of the tracking may be used by the robot 114 and/or by an operator of the system 100 or any component thereof. In some embodiments, the navigation system 118 can be used to track other components of the system (e.g., imaging device 112) and the system can operate without the use of the robot 114 (e.g., with the surgeon manually manipulating the imaging device 112 and/or one or more surgical tools, based on information and/or instructions generated by the navigation system 118, for example).

The navigation system 118 may provide navigation for a surgeon and/or a surgical robot during an operation. The navigation system 118 may be any now-known or future-developed navigation system, including, for example, the Medtronic StealthStation™ S8 surgical navigation system or any successor thereof. The navigation system 118 may include one or more cameras or other sensor(s) for tracking one or more reference markers, navigated trackers, or other objects within the operating room or other room in which some or all of the system 100 is located. The one or more cameras may be optical cameras, infrared cameras, or other cameras. In some embodiments, the navigation system 118 may comprise one or more electromagnetic sensors. In various embodiments, the navigation system 118 may be used to track a position and orientation (e.g., a pose) of the imaging device 112, the robot 114 and/or robotic arm 116, and/or one or more surgical tools (or, more particularly, to track a pose of a navigated tracker attached, directly or indirectly, in fixed relation to the one or more of the foregoing). The navigation system 118 may include a display for displaying one or more images from an external source (e.g., the computing device 102, imaging device 112, or other source) or for displaying an image and/or video stream from the one or more cameras or other sensors of the navigation system 118. In some embodiments, the system 100 can operate without the use of the navigation system 118. The navigation system 118 may be configured to provide guidance to a surgeon or other user of the system 100 or a component thereof, to the robot 114, or to any other element of the system 100 regarding, for example, a pose of one or more anatomical elements, whether or not a tool is in the proper trajectory, and/or how to move a tool into the proper trajectory to carry out a surgical task according to a preoperative or other surgical plan.

The database 130 may store information that correlates one coordinate system to another (e.g., one or more robotic coordinate systems to a patient coordinate system and/or to a navigation coordinate system). The database 130 may additionally or alternatively store, for example, one or more surgical plans (including, for example, pose information about a target and/or image information about a patient's anatomy at and/or proximate the surgical site, for use by the robot 114, the navigation system 118, and/or a user of the computing device 102 or of the system 100); one or more images useful in connection with a surgery to be completed by or with the assistance of one or more other components of the system 100; and/or any other useful information. The database 130 may be configured to provide any such information to the computing device 102 or to any other device of the system 100 or external to the system 100, whether directly or via the cloud 134. In some embodiments, the database 130 may be or comprise part of a hospital image storage system, such as a picture archiving and communication system (PACS), a health information system (HIS), and/or another system for collecting, storing, managing, and/or transmitting electronic medical records including image data.

The cloud 134 may be or represent the Internet or any other wide area network. The computing device 102 may be connected to the cloud 134 via the communication interface 108, using a wired connection, a wireless connection, or both. In some embodiments, the computing device 102 may communicate with the database 130 and/or an external device (e.g., a computing device) via the cloud 134.

The system 100 or similar systems may be used, for example, to carry out one or more aspects of any of the methods 400 and/or 500 described herein. The system 100 or similar systems may also be used for other purposes.

Figure 2:
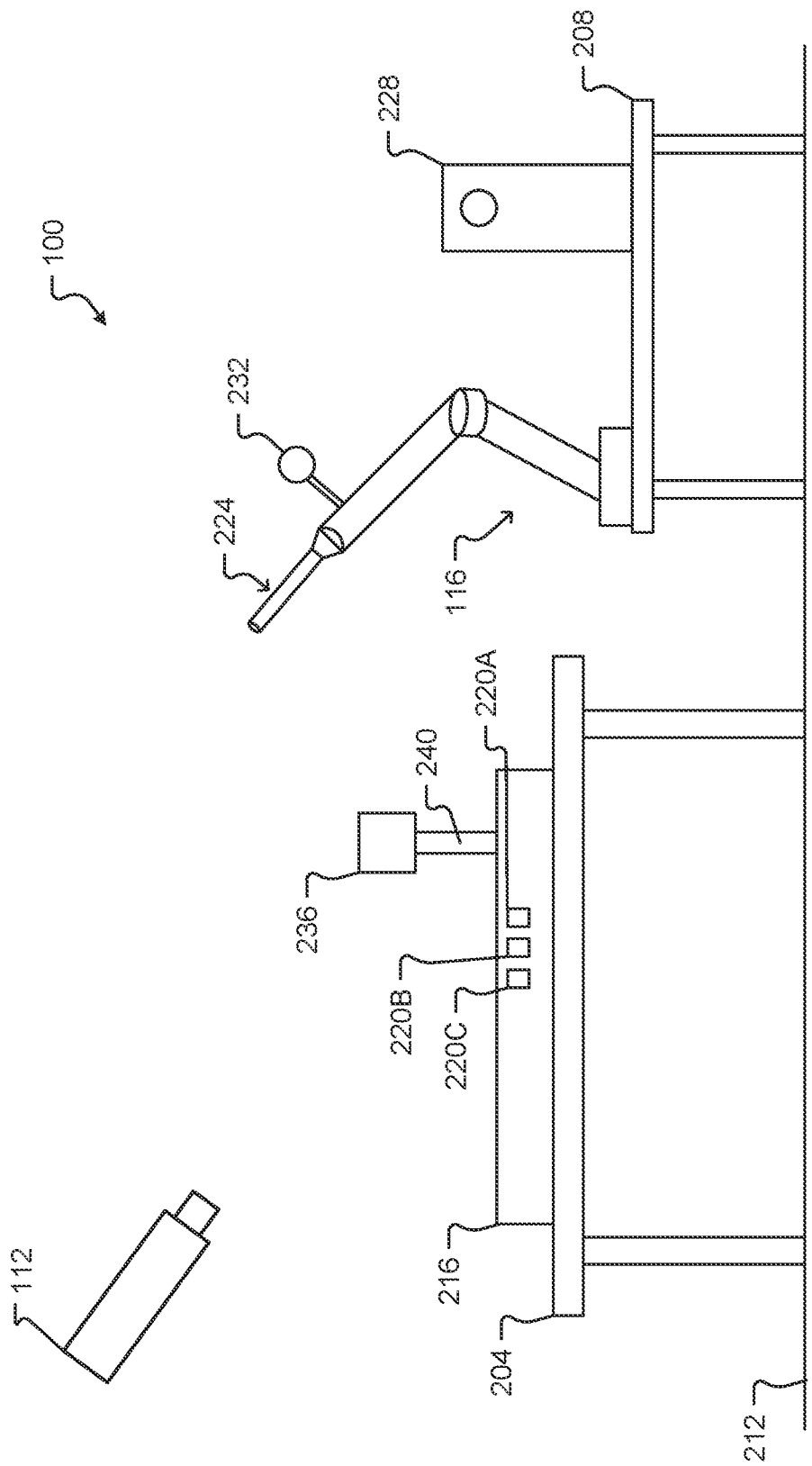
FIG. 2 is a block diagram of aspects of the system according to at least one embodiment of the present disclosure.
Figure 3A:
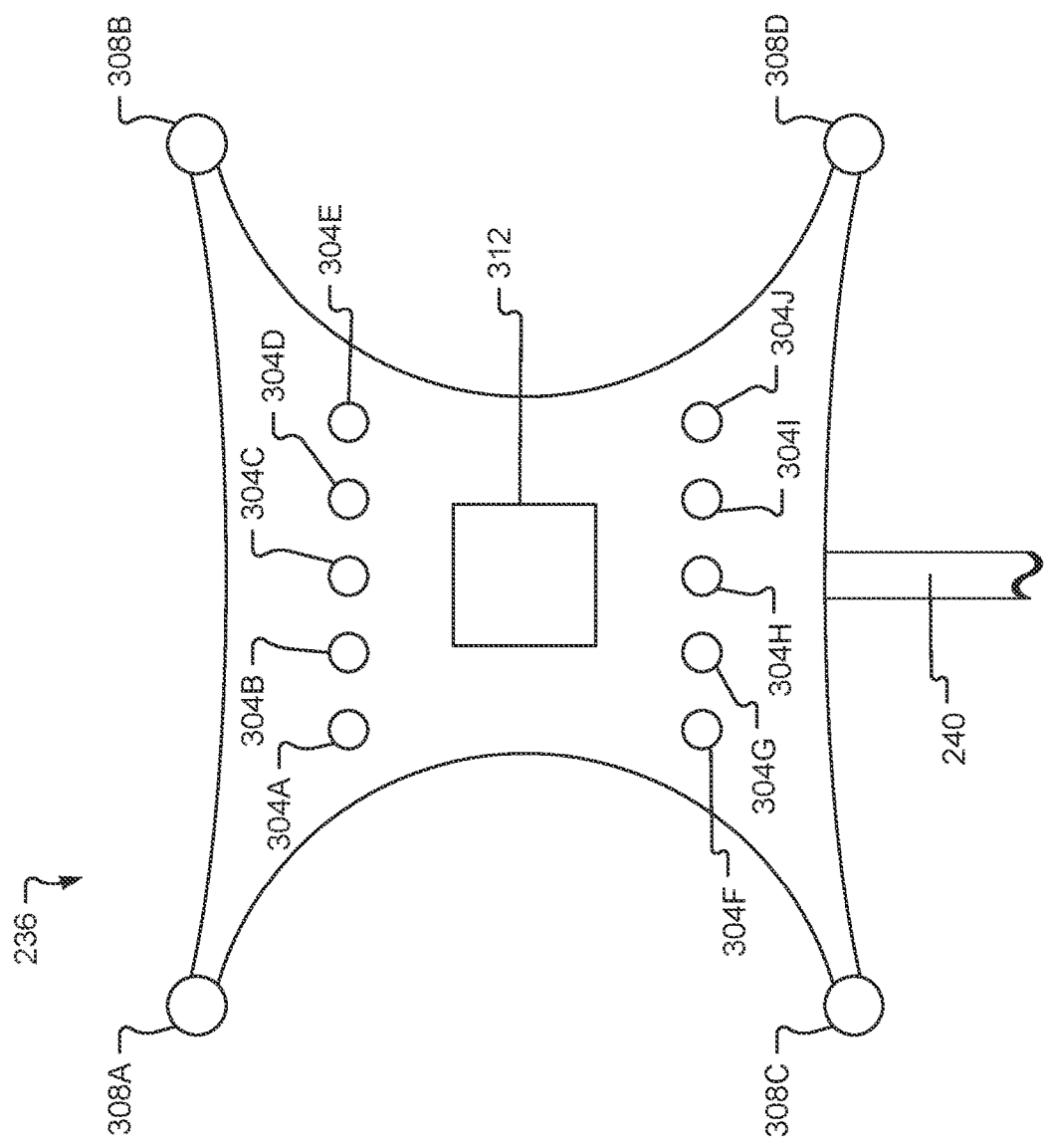
FIG. 3A depicts a navigation tracker according to at least one embodiment of the present disclosure.
Figure 3B:
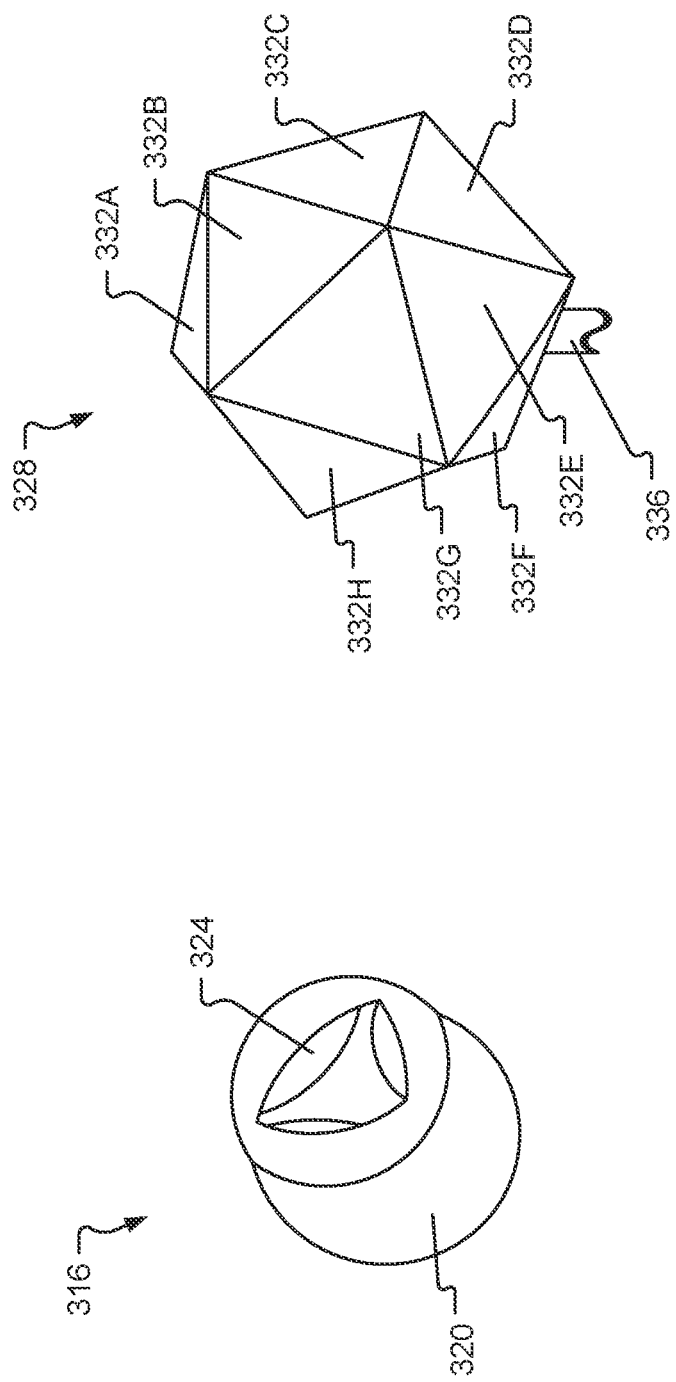
FIG. 3B depicts optical tracking markers according to at least one embodiment of the present disclosure.

FIGS. 2 and 3A-3B illustrate various aspects of the system 100 according to at least one embodiment of the present disclosure. FIG. 2 illustrates a surgical environment, such as an operating room, including a patient table 204 and a robotic table 208. The patient table 204 and the robotic table 208 may be positioned on a floor 212 of the surgical environment. In some embodiments, the patient table 204 and/or the robotic table 208 may be mobile and capable of being moved around the surgical environment. For example, the robotic table 208 may be or comprise a cart that moves relative to the patient table 204, allowing the robotic table 208 (and the robotic arm 116) to be brought in or otherwise introduced to the surgical environment after preparations for a surgery or surgical task have been performed. The robotic table 208 may be brought into the surgical environment after preoperative imaging has been performed, for example, to help lessen congestion of the surgical environment.

A patient 216 may be positioned on the patient table 204. The patient 216 may have anatomical elements 220A-220C, which may be the subject of the surgery or surgical procedure. For example, the surgical procedure may be a spinal fusion, and the anatomical elements 220A-220C may be vertebrae of the spine. In some embodiments, the patient 216 may be securely positioned on the patient table 204, such that the patient 216 and/or the anatomical elements 220A-220C cannot move relative to the patient table 204. While the discussion herein includes discussion of an anatomical element, it is to be understood that more or fewer anatomical elements may be present and may be identified and registered using methods discussed herein. Furthermore, it is to be understood that the methods and embodiments discussed herein may alternatively apply to a portion of an anatomical element (e.g., a spinous process of a vertebra).

The robotic table 208 includes the robotic arm 116 and an optical sensor 228. In some embodiments, the robotic table 208 may include additional or alternative components. For example, the optical sensor 228 may not be positioned on the robotic table 208, and may instead be disposed in another location in the surgical environment (e.g., on the floor 212, mounted on a wall, positioned on another surgical table, etc.). The robotic table 208 may include additional surgical components such as surgical tools, and may include one or more cabinets, drawers, trays, or the like to house the surgical components. In some embodiments, the robotic table 208 may be mechanically decoupled or may be otherwise detached from the patient table 204, such that the robotic table 208 and/or the surgical components thereon can move freely relative to the patient table 204, the patient 216, and/or the anatomical elements 220A-220C. In one embodiment, the robotic table 208 may be disposed a first distance from the patient table 204 (e.g., 0.5 meters (m), 1 m, 1.5 m, 2 m, etc.).

The optical sensor 228 may be or comprise a sensor capable of detecting and/or tracking optics-based targets (e.g., illuminated objects, visual targets, etc.). In some embodiments, the optical sensor 228 may be or comprise a laser tracker. The laser tracker may project or emit a laser that may reflect off one or more targets and back toward the laser tracker. The reflected light may be received and processed by the computing device 102 and/or the navigation system 118 and may enable the computing device 102 and/or the navigation system 118 to determine the relative distance and/or pose of the target relative to the laser tracker based on, for example, the angle, intensity, frequency, and/or the like of the returning laser. In one embodiment, the laser tracker may include a tracking system that tracks the target as the target moves, such that the laser tracker can continuously aim a laser at the target and receive the reflected laser. The information of the reflected laser may be processed (e.g., by the computing device 102, by the navigation system 118, etc.) to identify and determine a change in pose of the target as the target moves relative to the optical sensor 228. Alternatively, the optical sensor 228 may be or comprise a 3D camera capable of identifying one or more 3D optical tracking targets. The 3D camera may be able to identify the 3D optical tracking targets based on a number of faces, designs, or patterns displayed by the 3D optical tracking targets. For example, the 3D camera may identify the optical tracking target based on different QR codes displayed on each surface of the 3D optical tracking target. The processor 104 may receive the identified faces, and may determine (e.g., using transformations 124) the pose of the optical tracking target within the surgical environment. For example, the identified faces may be compared to a predetermined (e.g., preoperative) pose of the surfaces, with the changes in pose of each faces used to determine the pose of the optical tracking target.

In some embodiments, the optical sensor 228 may be disposed proximate the robotic arm 116 (e.g., disposed 0.1 m, 0.2 m, 0.5 m, 1 m, 1.5 m, 2 m, etc. away from the robotic arm 116), such that the optical sensor 228 can view and track the robotic arm 116 in addition to any optical-based targets in the environment. Alternatively, the optical sensor 228 may be disposed within a portion of the robotic arm 116 (e.g., within the end effector 224). In such embodiments, the optical sensor 228 may be disposed in a predetermined configuration relative to the robotic arm 116, such that the pose of the robotic arm 116 may be determined based on internal readings generated by a sensor (e.g., using gyroscopes, accelerometers, etc.).

The robotic arm 116 may include an end effector 224. The end effector 224 may be or comprise a receptacle, mount, gripper, or other mechanical interface for interacting with a surgical tool or instrument. For example, the end effector 224 may interface with a surgical tool to manipulate a surgical tool (whether based on guidance from the navigation system 118 or not) to accomplish or to assist with a surgery or surgical procedure or task. In some embodiments, the end effector 224 may have an interchangeable interface, such that different surgical tools with different connection capabilities can be used with the end effector 224. For example, the end effector 224 may have a first interface to permit a surgical drill to be attached thereto and a second interface to hold a surgical screw. In some embodiments, the end effector 224 may include a tracking marker 232 disposed thereon. The positioning of the tracking marker 232 on the end effector 224 may enable the imaging devices 112 and/or the optical sensor 228 to track the pose of the end effector 224. For example, the tracking marker 232 may be a cube with a different QR code on each face, such that the optical sensor 228 track the tracking marker 232 and can identify each face of the tracking marker 232, and the computing device 102 and/or the navigation system 118 can use the identified faces to determine a pose of the tracking marker 232. Based on the pose of the tracking marker 232 and a predetermined position of the tracking marker 232 on the end effector 224, the computing device 102 and/or the navigation system 118 may use the pose of tracking marker 232 to determine a pose of the end effector 224 or, more generally, a pose of the robotic arm 116.

A navigation tracker 236 may be disposed on or proximate to the patient 216. In some embodiments, the navigation tracker 236 may be attached to the patient 216 using an attachment mechanism 240. The attachment mechanism 240 may be or comprise, for example, a clamp attached to a spinous process of a vertebra, a threaded rod capable of screwing into the patient table 204, or the like. In some embodiments, the attachment mechanism 240 may be connected to the patient 216 such that any movement of the patient 216 and/or the anatomical elements 220A-220C may result in a corresponding movement of the navigation tracker 236. A movement of a first anatomical element 220A in a first distance in a first direction may, for example, cause the navigation tracker 236 attached to the first anatomical element 220A to move the first distance in the first direction as well.

With reference to FIG. 3A, the navigation tracker 236 may include navigation elements of different types to be used with different navigation and registration processes. In one embodiment, the navigation tracker 236 may include navigation elements of a first type, navigation elements of a second type, and navigation elements of a third type. Each of the different types of navigation elements may be capable of being tracked, captured, or otherwise identified by a corresponding imaging device of the same type. Additionally or alternatively, the navigation elements may not appear to or be recognized by an imaging device of a different type. For example, a navigation element of a first type may be a fluoroscopic marker capable of being detected in fluoroscopic imaging, but may not appear in imaging associated with, or may not be recognized by, an optical sensor.

In some embodiments, the navigation elements of the first type may be or comprise one or more fluoroscopic markers 304A-304J. In one embodiment, the fluoroscopic markers 304A-304J may be or comprise metal spheres disposed on the navigation tracker 236. In other embodiments, the shape and size of the fluoroscopic markers 304A-304J may vary depending, for example, on the surgery or surgical procedure, the accuracy requirements of the system 100, the type of navigation tracker 236, or the like. The fluoroscopic markers 304A-304J may be or comprise radiopaque elements (e.g., elements that appear opaque on fluoroscopic imaging or other radiation-based imaging), such that the fluoroscopic markers 304A-304J can be identified in fluoroscopic images. In other words, the fluoroscopic markers 304A-304J may appear in a fluoroscopic image along with the depicted patient anatomy, enabling registration (e.g., using registration 128) from the patient anatomy to the fluoroscopic markers 304A-304J, and/or vice versa. As discussed in greater detail below, to complete a registration from the fluoroscopic markers 304A-304J to the anatomical elements, the computing device 102 may receive the image data associated with one or more fluoroscopic images and may use image processing 120 to identify the patient anatomy and each of the fluoroscopic markers 304A-304J. The computing device 102 may then use a registration 128 to determine a position of each of the fluoroscopic markers 304A-304J relative to the patient anatomy. In some embodiments, the fluoroscopic markers 304A-304J may be disposed in a predetermined configuration or pattern. For instance, as depicted in FIG. 3A, fluoroscopic markers 304A-304E are disposed on an upper portion of the navigation tracker 236, while fluoroscopic markers 304F-304J are disposed on a lower portion of the navigation tracker 236. In some embodiments, the fluoroscopic markers may be evenly or uniformly spaced apart. In some embodiments, the pose of each fluoroscopic marker of the fluoroscopic markers 304A-304J relative to one or more locations of the navigation tracker 236 (such as relative to the other fluoroscopic markers fluoroscopic markers 304A-304J or relative to other navigation elements disposed on the navigation tracker 236) may be saved or stored in the database 130.

The navigation tracker 236 may also include navigation elements of a second type, such as navigation markers 308A-308D. The navigation markers 308A-308D may be or comprise fiducial markers capable of being recognized by the imaging device 112 of the navigation system 118. For example, the navigation markers 308A-308D may be or comprise spheres disposed on corner points or the outer perimeter of the navigation tracker 236. In some embodiments, the navigation markers 308A-308D may include more or fewer markers than those shown in FIG. 3A, and may additionally or alternatively be disposed in a different orientation. For example, in some embodiments the navigation markers 308A-308D may comprise a plurality of navigation markers disposed in a cross pattern. In embodiments where both the navigation markers 308A-308D and the fluoroscopic markers 304A-304J are similarly shaped (e.g., both sets of markers include spheres), the navigation markers 308A-308D may be distinguished from the fluoroscopic markers 304A-304J by the navigation system 118 based on the size of the sphere, the reflectiveness of the sphere when illuminated with light, the position of the spheres on the navigation tracker 236, combinations thereof, and/or the like. In some embodiments, the navigation markers 308A-308D may be or comprise active markers (e.g., LEDs) that are illuminated when viewed by the imaging device 112 of the navigation system 118.

The navigation tracker 236 may also include a navigation element of a third type, such as an optical sensor tracker target 312. The optical sensor tracker target 312 may be a target capable of being tracked by the optical sensor 228. By tracking the position of the optical sensor tracker target 312, the navigation system 118 can determine the pose of the navigation tracker 236 relative to the optical sensor 228 and/or the robotic arm 116. In some embodiments, the optical sensor tracker target 312 may be disposed in a predetermined position on the navigation tracker 236. In one embodiment, the optical sensor tracker target 312 may be centered in the middle of the navigation tracker 236.

In some embodiments, the optical sensor tracker target 312 may be used to monitor the position of patient anatomy relative to the robotic arm 116. For example, a physician or other member of the surgical staff may accidently bump the patient table 204, or the anatomical elements 220A-220C may otherwise move relative to the robotic arm 116. The movement of the anatomical elements 220A-220C may cause the navigation tracker 236 and the optical sensor tracker target 312 to also move relative to the robotic arm 116 from a first pose to a second pose. To measure this movement, the change in pose of the optical sensor tracker target 312 can be identified by the optical sensor 228, and a new pose of the optical sensor tracker target 312 can be determined based on information generated by the optical sensor 228.

Turning to FIG. 3B, various optical sensor trackers are shown in accordance with embodiments of the present disclosure. In some embodiments, the optical sensor tracker target 312 may be or comprise a laser target 316. The laser target 316 may be an optical target that includes a base 320 and mirrors 324. The base 320 may enable the laser target 316 to be attached or affixed to the navigation tracker 236. The mirrors 324 may bend the laser or other light generated by the optical sensor 228 and reflect the light back to the optical sensor 228 to enable the optical sensor 228 to determine the pose of the laser target 316. In some embodiments, the laser target 316 may be capable of generating and emitting one or more signals (e.g., electronic signals, RF signals, etc.) when light emitted by the optical sensor 228 strikes the mirrors 324. The one or more signals may be received by the computing device 102, the navigation system 118, and/or the optical sensor 228, and may be further processed to determine the pose of the laser target 316. For example, the laser target 316 may emit a signal containing information related to the frequency, intensity, and/or incoming direction of light that strikes the laser target 316. This information may be used along with information about the initial light generated by the optical sensor 228 to determine the pose of the laser target 316 relative to the optical sensor 228. In some embodiments, the laser target 316 may be or comprise one or more metals or metal alloys, such that the laser target 316 may be radiopaque.

In some embodiments, the optical sensor tracker target 312 may be or comprise a 3D target 328. The 3D target 328 may include a base 336 that may be used to attach the 3D target 328 to one or more surfaces, instruments, or trackers (e.g., to the navigation tracker 236, to the end effector 224 of the robotic arm 116, etc.). The 3D target 328 may also include faces 332A-332H that enable a 3D camera or other imaging device to identify the 3D target 328. In some embodiments, each of the faces 332A-332H may contain a unique pattern displayed, such that each face can be identified by the 3D camera. For instance, each face may display a separate QR code, label, or other tag. When the 3D camera views or captures images of the 3D target 328, each face as seen by the camera or depicted in the image can be identified. In some embodiments, the 3D target 328 may have a predetermined configuration, such that any movement of the 3D target 328 may be identified and captured by the 3D camera. In such embodiments, an additional 3D target 328 may be disposed on the robotic arm 116 (e.g., on the end effector 224 of the robotic arm 116), such that movements of the robotic arm 116 can be captured by the 3D camera.

In some embodiments, the fluoroscopic markers 304A-304J, the navigation markers 308A-308D, and the optical sensor tracker target 312 may be disposed on the navigation tracker 236 in a predetermined configuration. The predetermined configuration may ensure that the navigation elements are disposed in a fixed orientation on the navigation tracker, which may allow the computing device 102 and/or the processor 104 to know or easily determine the pose of any fluoroscopic marker of the fluoroscopic markers 304A-304J, any navigation marker of the navigation markers 308A-308D, and/or the optical sensor tracker target 312 relative to any other navigation element on the navigation tracker 236, and/or to a fixed point (e.g., a point on the outer perimeter, a center point, etc.) on the navigation tracker 236. In some embodiments, the predetermined configuration may be tied to a component or part number (e.g., a first navigation tracker may have a different configuration of navigation elements than a second navigation tracker) of the navigation tracker 236. In some embodiments, predetermined configuration information (e.g., the relative distances and directions of any one navigation element to some or all of the other navigation elements) may be stored in the database 130, and may be used in performing one or more registrations.

Figure 4:
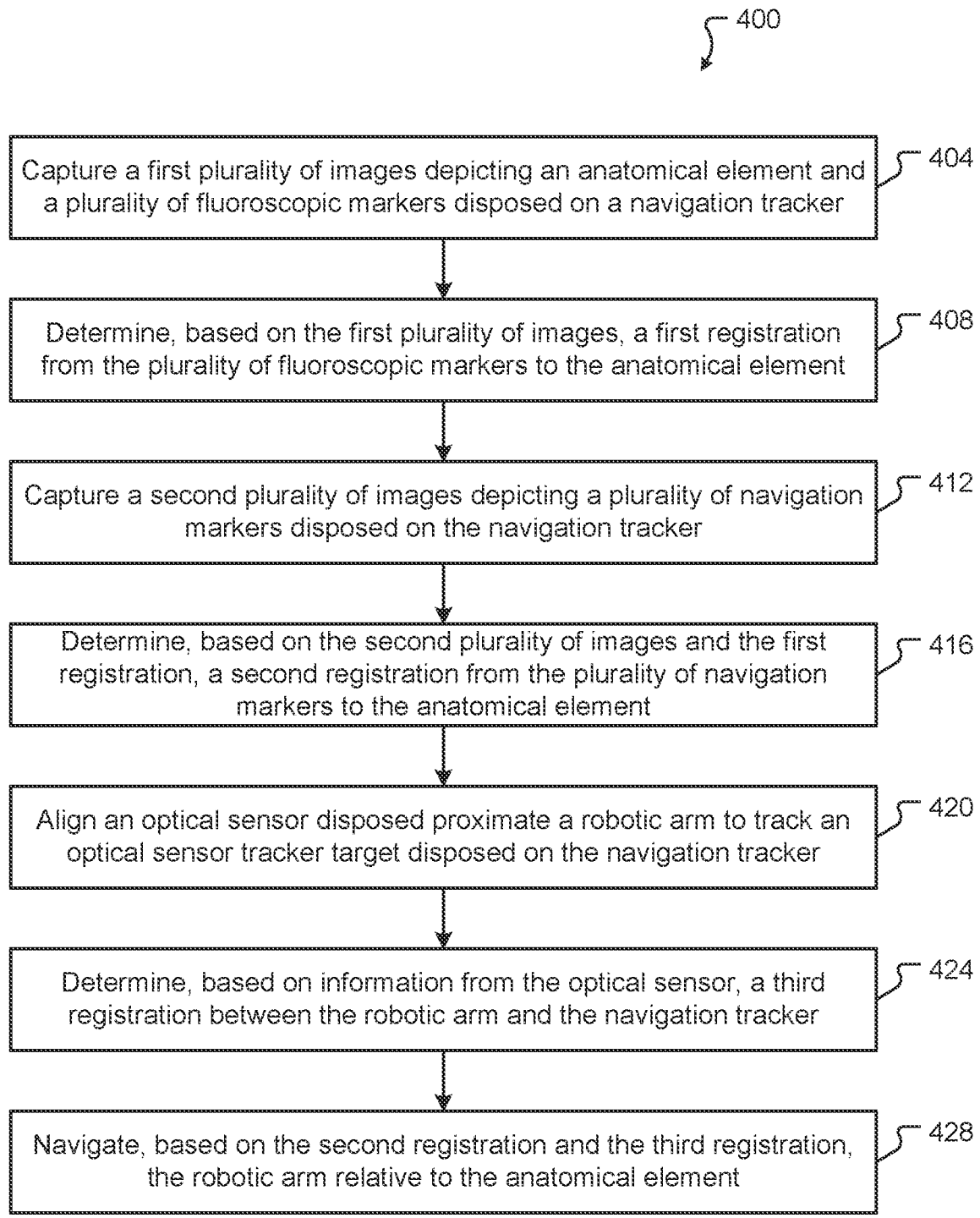
FIG. 4 is a flowchart according to at least one embodiment of the present disclosure.

FIG. 4 depicts a method 400 that may be used, for example, to establish a virtual bone mount and navigate the robot relative to patient anatomy using the virtual bone mount.

The method 400 (and/or one or more steps thereof) may be carried out or otherwise performed, for example, by at least one processor. The at least one processor may be the same as or similar to the processor(s) 104 of the computing device 102 described above. The at least one processor may be part of a robot (such as a robot 114) or part of a navigation system (such as a navigation system 118). A processor other than any processor described herein may also be used to execute the method 400. The at least one processor may perform the method 400 by executing elements stored in a memory such as the memory 106. The elements stored in memory and executed by the processor may cause the processor to execute one or more steps of a function as shown in method 400. One or more portions of a method 400 may be performed by the processor executing any of the contents of memory, such as an image processing 120, a segmentation 122, a transformation 124, and/or a registration 128.

The method 400 comprises capturing a first plurality of images depicting an anatomical element and a plurality of fluoroscopic markers disposed on a navigation tracker (step 404). The anatomical element may be similar to or the same as the first anatomical element 220A, the second anatomical element 220B, or the third anatomical element 220C. The navigation tracker may be similar to or the same as the navigation tracker 236, and the plurality of fluoroscopic markers may be similar to or the same as the fluoroscopic markers 304A-304J. In some embodiments, the fluoroscopic markers 304A-304J may be disposed in a predetermined configuration on the navigation tracker 236. The first plurality of images may be or comprise a plurality of fluoroscopic images or fluoroscopic image data captured by a fluoroscopic imaging device (e.g., an X-ray source and an X-ray detector). In some embodiments, the images may be captured using an O-arm or other imaging device 112. The fluoroscopic imaging device may be positioned at a predetermined location when each image is captured, and each captured image of the first plurality of images may depict the fluoroscopic markers 304A-304J and the navigation tracker 236 in a different pose (e.g., a different position and/or orientation). In some embodiments, the first plurality of images may be captured preoperatively (e.g., before the surgery or surgical procedure begins).

The method 400 also comprises determining, based on the first plurality of images, a first registration from the plurality of fluoroscopic markers to the anatomical element (step 408). The first registration may be or comprise a map from the coordinates associated with one or more of the fluoroscopic markers 304A-304J in a first coordinate system to a second coordinate system containing the coordinates of the anatomical element, or vice versa. In some embodiments, the registration may transform both sets coordinates into a third coordinate system, such as a coordinate system used by the robotic arm. In some embodiments, the plurality of images may depict additional anatomical elements (e.g., multiple vertebrae of the spine), and the first registration may include mapping coordinates associated with each of the additional anatomical elements into a common coordinate system.

In some embodiments, the first registration may be determined using image processing 120 and one or more registrations 128. The image processing 120 may be used to identify the plurality of fluoroscopic markers and the anatomical element in each image of the first plurality of images. In some embodiments, the image processing 120 may be or comprise one or more machine learning and/or artificial intelligence models that receive each image as an input and output coordinates associated with each identified fluoroscopic marker and anatomical element. The registration 128 may use the determined coordinates associated with each identified fluoroscopic marker and anatomical element to determine a pose of each fluoroscopic marker relative to the anatomical element, and may transform the coordinates associated with each fluoroscopic marker from a first coordinate system to a second coordinate system. For example, the registration 128 may take coordinates associated with each of the identified fluoroscopic markers and map the coordinates into a coordinate system associated with the anatomical element (or vice versa). Additionally or alternatively, the registration 128 may map the fluoroscopic marker coordinates and the anatomical element coordinates into a third coordinate system (e.g., a robotic space coordinate system) shared by other surgical tools or components in a surgical environment.

The method 400 also comprises capturing a second plurality of images depicting a plurality of navigation markers disposed on the navigation tracker (step 412). The plurality of navigation markers may be the same as or similar to the navigation markers 308A-308D. In some embodiments, the navigation markers 308A-308D may be disposed on the navigation tracker 236 in a predetermined configuration (e.g., along an outer perimeter of the navigation tracker 236, on the corners of the navigation tracker 236, etc.). The second plurality of images may be images of a different type than those captured by the first plurality of images, such that the appearance of the navigation markers and/or the fluoroscopic markers is different in the second plurality of images. While the plurality of navigation markers may not appear in the first plurality of images, for example, the plurality of navigation markers may appear in the second plurality of images. In one embodiment, the second plurality of images may be images or image data captured by a navigation camera (e.g., a 3D camera, an ultrasound camera, or other camera). Each captured image of the second plurality of images may depict the navigation markers in different poses, and the pose of the navigation camera capturing the image may be known (e.g., based on a predetermined image capture navigation path).

The method 400 also comprises determining, based on the second plurality of images and the first registration, a second registration from the plurality of navigation markers to the anatomical element (step 416). The second registration may be or comprise a map of coordinates associated with each of the navigation markers 308A-308D to a coordinate system associated with the anatomical element, or vice versa. In some embodiments, the registration 128 may transform the coordinates associated with each of the navigation markers 308A-308D into a different coordinate system shared by the fluoroscopic markers 304A-304J and the anatomical element (e.g., the robotic space coordinate system).

In some embodiments, image processing 120 and one or more registrations 128 may be used to identify the navigation markers 308A-308D in the second plurality of images, determine coordinates associated with each of the navigation markers 308A-308D, and map the coordinates to the coordinate system shared by the fluoroscopic markers 304A-304J, the anatomical element, and the robotic arm 116. The image processing 120 may be or comprise one or more machine learning and/or artificial intelligence models that receive each image as an input and output coordinates associated with each identified navigation marker. The second registration may then be determined based on the coordinates of each of the navigation markers relative to the fluoroscopic markers 304A-304J and a predetermined configuration of how the navigation markers 308A-308D and the fluoroscopic markers 304A-304J are disposed on the navigation tracker 236. For instance, the registration 128 may use information about the predetermined configuration to map the identified coordinates of the navigation markers 308A-308D to the coordinate system shared by the fluoroscopic markers 304A-304J and the anatomical element.

Additionally or alternatively, the registration 128 may use the predetermined configuration of the fluoroscopic markers 304A-304J disposed on the navigation tracker 236 to map coordinates associated with the navigation tracker 236 into the shared coordinate system. In other words, the registration 128 may be used to determine a pose of the navigation tracker 236 relative to the anatomical element. The registration 128, for example, may receive the coordinates for each of the fluoroscopic markers 304A-304J, and one or more coordinates of the navigation tracker 236 (e.g., coordinates associated with the outer perimeter of the navigation tracker 236, coordinates associated with a center point of the navigation tracker 236, etc.), and may map the navigation tracker 236 coordinates into to a coordinate system containing the fluoroscopic markers 304A-304J and/or to the shared coordinate system. The coordinates for the navigation tracker 236 in the shared coordinate system may be determined based on the determined pose of the navigation markers 308A-308D and the predetermined configuration of the navigation markers 308A-308D disposed on the navigation tracker 236.

The method 400 also comprises aligning an optical sensor disposed proximate a robotic arm to track an optical sensor tracker target disposed on the navigation tracker (step 420). The robotic arm may be similar to or the same as the robotic arm 116. The optical sensor may be similar to or same as the optical sensor 228 and the optical sensor tracker target may be similar to or the same as the optical sensor tracker target 312. The optical sensor 228 may be pointed at the optical sensor tracker target 312, such that the optical sensor tracker target 312 can be identified and a pose of the optical sensor tracker target 312 can be determined. For example, the optical sensor 228 may be or comprise a laser tracker that emits a laser that is captured by the optical sensor tracker target 312 (e.g., the optical sensor tracker target 312 may be or comprise a laser target 316). Alternatively, the optical sensor 228 may be or comprise a 3D camera, and the optical sensor tracker target 312 may be or comprise a 3D target 328. In some embodiments, the optical sensor 228 may automatically identify the optical sensor tracker target 312 (e.g., the processor 104 may cause the optical sensor 228 to search the surrounding area until the optical sensor tracker target 312 is identified), or the optical sensor 228 may alternatively be aligned manually (e.g., by a physician, by a member of the surgical staff, etc.). In some embodiments, the alignment of the optical sensor 228 with the optical sensor tracker target 312 may occur after preoperative images (e.g., the first plurality of images and/or the second plurality of images) are captured.

The method 400 also comprises determining, based on information from the optical sensor, a third registration between the robotic arm and the navigation tracker (step 424). The step 424 may be described in greater detail with reference to the method 500 of FIG. 5. The optical sensor 228 may capture information related to the pose of the optical sensor tracker target 312, and the information may be used to determine the third registration between the robotic arm 116 and the navigation tracker 236. In some embodiments, the information may be based on the pose, distance, position, etc. of the optical sensor tracker target 312 (and by extension the navigation tracker 236) relative to the optical sensor 228. In some embodiments, the optical sensor 228 may be disposed a known distance from the robotic arm 116, such that the information about the optical sensor tracker target 312 can be used by registration 128 to generate the third registration.

The method 400 also comprises navigating, based on the second registration and third registration, the robotic arm relative to the anatomical element (step 428). The second registration and third registration may be used to move the robotic arm 116 to, for example, perform one or more surgical tasks on the anatomical element (e.g., a drilling procedure, an implant procedure, a screwing procedure, an incision procedure, etc.). The navigation system 118 may know, based on the second registration, a pose of the navigation tracker 236 relative to the anatomical element, and may also know, based on the third registration, the pose of the robotic arm relative to the navigation tracker 236. The navigation system 118 may then be able to adjust the pose of the robotic arm 116 relative to the anatomical element.

As the robotic arm 116, for example, moves from a first pose to a second pose, the optical sensor 228 may continuously track the optical sensor tracker target 312 and generate data related thereto. The computing device 102 and/or the navigation system 118 may process the data about the change in pose of the optical sensor tracker target 312 as seen by the optical sensor 228. The computing device 102 and/or the navigation system 118 may alternatively process data about the change in pose of the robotic arm 116 and/or the optical sensor tracker target 312 based on, for example, the tracking marker 232 disposed on the robotic arm 116 and the 3D target 328 disposed on the navigation tracker 236, respectively.

In some embodiments, the third registration may be updated based on unexpected or unplanned movement of the navigation tracker 236 (or components thereof) relative to the robotic arm 116 (or components thereof), or vice versa. For instance, the patient table 204 may be accidently bumped or moved, and the navigation tracker 236 may move unexpectedly relative to the robotic arm 116. This move may be reflected in the data generated by the optical sensor 228 (e.g., the determinations made by the computing device 102 indicate that the navigation tracker 236 is no longer in the planned or desired pose). The computing device 102 and/or the navigation system 118 may generate an alert to warn that the third registration is no longer accurate (e.g., a warning message rendered to the user interface 110), and the step 424 may be performed again to generate a new registration between the robotic arm 116 and the navigation tracker 236.

The present disclosure encompasses embodiments of the method 400 that comprise more or fewer steps than those described above, and/or one or more steps that are different than the steps described above.

Figure 5:
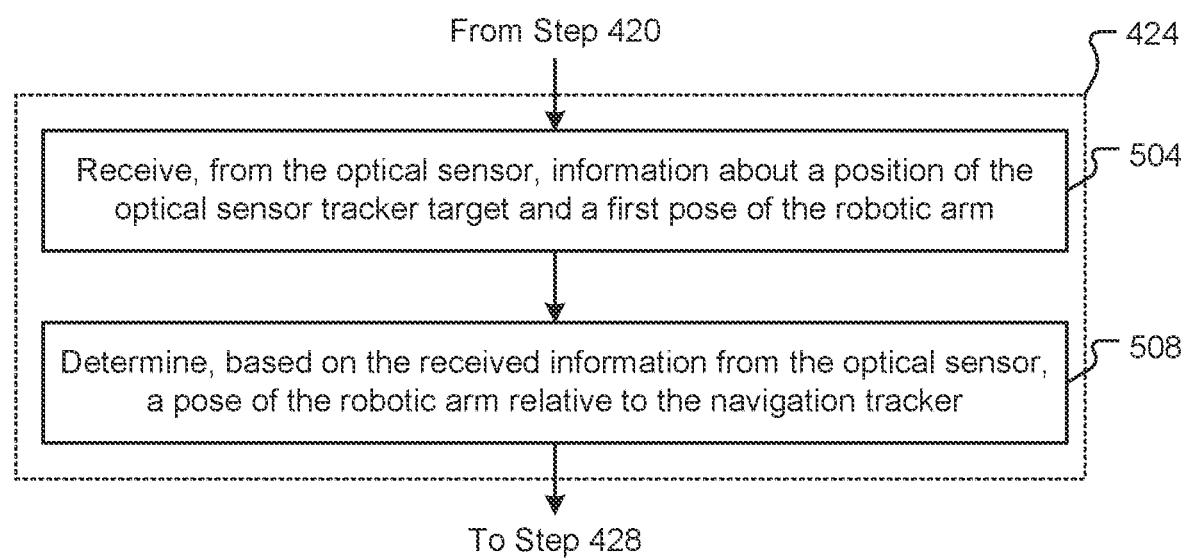
FIG. 5 is a flowchart according to at least one embodiment of the present disclosure.

FIG. 5 depicts a method 500 that may be used, for example, to determine a registration between a robotic arm and a navigation tracker based on measurements about a tracker made by a sensor. In some embodiments, the method 500 may performed as part of the step 424 of determining the registration between the robotic arm and the navigation tracker.

The method 500 (and/or one or more steps thereof) may be carried out or otherwise performed, for example, by at least one processor. The at least one processor may be the same as or similar to the processor(s) 104 of the computing device 102 described above. The at least one processor may be part of a robot (such as a robot 114) or part of a navigation system (such as a navigation system 118). A processor other than any processor described herein may also be used to execute the method 500. The at least one processor may perform the method 500 by executing elements stored in a memory such as the memory 106. The elements stored in memory and executed by the processor may cause the processor to execute one or more steps of a function as shown in method 500. One or more portions of a method 500 may be performed by the processor executing any of the contents of memory, such as an image processing 120, a segmentation 122, a transformation 124, and/or a registration 128.

The method 500 comprises receiving, from the optical sensor, information about a position of an optical sensor tracker target and a first pose of the robotic arm (step 504). In some embodiments, the optical sensor 228 may generate information about the pose of the optical sensor tracker target 312 (e.g., when the optical sensor 228 is disposed on or within the robotic arm 116) based on how light emitted from the optical sensor 228 interacts with the optical sensor tracker target 312. For example, the optical sensor 228 may be or comprise a laser tracker that emits light that hits the optical sensor tracker target 312 (which may be or comprise the laser target 316). Information about the intensity, frequency, angle, etc. of the light contacting the laser target 316 may be generated and sent to the computing device 102 and/or the computing device 102. Similarly, information about the first pose of the robotic arm 116 may be generated by a sensor (e.g., a gyroscope, an accelerometer, combinations thereof, and/or the like) disposed within or proximate the robotic arm 116. The measured movement may be used, along with a known predetermined pose (e.g., a pose before the robotic arm 116 began moving), to determine the first pose of the robotic arm 116.

In some embodiments, the optical sensor 228 may view both the optical sensor tracker target 312 and the tracking marker 232 disposed on the robotic arm 116. In such embodiments, the optical sensor 228 may include a 3D camera capable of identifying the optical sensor tracker target 312 (which may be the 3D target 328) and the tracking marker 232 disposed on the robotic arm 116. The information may be captured in the form of one or more images or a continuous stream of data depicting both the 3D target 328 and the tracking marker 232 and the relative locations of each. In some embodiments, the optical sensor 228 may continuously generate the information as the robotic arm 116 moves while performing a surgical task.

The method 500 also comprises determining, based on the received information from the optical sensor, a pose of the robotic arm relative to the navigation tracker (step 508). The registration 128 may be used to determine the pose of the robotic arm 116 relative to the navigation tracker 236. When the optical sensor 228 is only tracking the laser target 316, one or more transformations 124 may be used to process the measured movement of the robotic arm (e.g., movement measured by an accelerometer) to determine coordinates associated with of the robotic arm 116 in a first coordinate system. The registration 128 may then be used to map the coordinates of the robotic arm 116 into a coordinate system associated with the navigation tracker 236. In some embodiments, the registration 128 may map the coordinates associated with the navigation tracker 236 and the coordinates associated with the robotic arm 116 into a third coordinate system, such that the computing device 102 and/or the navigation system 118 have information about the pose of the robotic arm 116 relative to the navigation tracker 236.

In embodiments where the optical sensor 228 tracks both the 3D target 328 and the robotic arm 116 (based on relative movement of the tracking marker 232), image processing may be used to identify each of the 3D target 328 and the tracking marker 232 (e.g., using QR codes on each face of the optical sensor tracker target 312 and the tracking marker 232). One or more transformations 124 may then be used, along with information (e.g., from a database 130) describing an initial pose of each of the 3D target 328 and the tracking marker 232 to determine the new pose of the optical sensor tracker target 312 and/or the tracking marker 232. The registration 128 may then map the coordinates of the tracking marker 232 into a coordinate system describing the 3D target 328, or vice versa. In some embodiments, the registration 128 may map coordinates associated with the 3D target 328 and coordinates associated with the tracking marker 232 into a common coordinate system, such that the computing device 102 and/or the navigation system 118 have information about the pose of the robotic arm 116 relative to the navigation tracker 236.

In some embodiments, the steps 504 and 508 may be repeated, as mentioned above, whenever the computing device 102 and/or the navigation system 118 determines that the third registration between the robotic arm 116 and the navigation tracker 236 is inaccurate or no longer valid. In some embodiments, when the third registration is no longer accurate, the third registration may be recalculated, while the first registration and/or the second registration may remain in use (e.g., the anatomical element has not moved relative to the navigation tracker 236).

The present disclosure encompasses embodiments of the method 500 that comprise more or fewer steps than those described above, and/or one or more steps that are different than the steps described above.

As noted above, the present disclosure encompasses methods with fewer than all of the steps identified in FIGS. 4 and 5 (and the corresponding description of the methods 400 and 500), as well as methods that include additional steps beyond those identified in FIGS. 4 and 5 (and the corresponding description of the methods 400 and 500). The present disclosure also encompasses methods that comprise one or more steps from one method described herein, and one or more steps from another method described herein. Any correlation described herein may be or comprise a registration or any other correlation.

The foregoing is not intended to limit the disclosure to the form or forms disclosed herein. In the foregoing Detailed Description, for example, various features of the disclosure are grouped together in one or more aspects, embodiments, and/or configurations for the purpose of streamlining the disclosure. The features of the aspects, embodiments, and/or configurations of the disclosure may be combined in alternate aspects, embodiments, and/or configurations other than those discussed above. This method of disclosure is not to be interpreted as reflecting an intention that the claims require more features than are expressly recited in each claim. Rather, as the following claims reflect, inventive aspects lie in less than all features of a single foregoing disclosed aspect, embodiment, and/or configuration. Thus, the following claims are hereby incorporated into this Detailed Description, with each claim standing on its own as a separate preferred embodiment of the disclosure.

Moreover, though the foregoing has included description of one or more aspects, embodiments, and/or configurations and certain variations and modifications, other variations, combinations, and modifications are within the scope of the disclosure, e.g., as may be within the skill and knowledge of those in the art, after understanding the present disclosure. It is intended to obtain rights which include alternative aspects, embodiments, and/or configurations to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A system, comprising:
a processor; and
a memory storing data thereon that, when processed by the processor, cause the processor to:
 determine, based on a navigation element of a first type and a navigation element of a second type both disposed on a navigation tracker, a registration between the navigation tracker and an anatomical element;

determine, based on a navigation element of a third type disposed on the navigation tracker, another registration between a robotic arm and the navigation tracker; and navigate, based on the registration and the another registration, the robotic arm relative to the anatomical element.

2. The system of claim 1, wherein the navigation element of the first type, the navigation element of the second type, and the navigation element of the third type are disposed on the navigation tracker in a predetermined configuration.

3. The system of claim 2, wherein the navigation element of the third type comprises a first optical tracking marker tracked by a third imaging device, and wherein determining the another registration comprises the processor:

receiving, from the third imaging device, information about a first location of the first optical tracking marker and a first pose of the robotic arm; and determining, based on the information about the first location of the first optical tracking marker and the first pose of the robotic arm, a position of the robotic arm relative to the first optical tracking marker.

4. The system of claim 3, wherein the navigation element of the first type includes a plurality of fluoroscopic markers capable of being detected by a first imaging device, and wherein determining the registration comprises the processor:

receiving, from the first imaging device, a plurality of images depicting the plurality of fluoroscopic markers and the anatomical element; and determining, based on the plurality of images, a position of each fluoroscopic marker of the plurality of fluoroscopic markers relative to the anatomical element.

5. The system of claim 4, wherein the navigation element of the second type includes a plurality of navigation markers capable of being detected by a second imaging device, and wherein determining the registration further comprises the processor:

receiving, from the second imaging device, information about a position of each navigation marker of the plurality of navigation markers; and determining, based on the information about the position of each navigation marker and the predetermined configuration, a position of each navigation marker relative to the anatomical element.

6. The system of claim 5, wherein the robotic arm includes a second optical tracking marker, and wherein the third imaging device tracks the second optical tracking marker.

7. The system of claim 6, wherein the first imaging device comprises a fluoroscopic imaging device, wherein the second imaging device comprises a navigation camera, and wherein the third imaging device comprises a laser tracker.

8. The system of claim 5, wherein the navigation tracker is disposed on a patient table, wherein the robotic arm is disposed on a second table a first distance from the patient table, and wherein the third imaging device is disposed a second distance from the robotic arm.

9. The system of claim 8, wherein the first imaging device comprises an O-arm, wherein the second imaging device comprises a navigation camera, and wherein the third imaging device comprises a three-dimensional (3D) camera.

10. A system, comprising:

a robotic arm disposed a first distance from a patient bed;

a processor; and a memory storing data thereon that, when processed by the processor, cause the processor to:

determine, based on a navigation element of a first type and a navigation element of a second type both disposed on a navigation tracker, a first registration between the navigation tracker and an anatomical element;

determine, based on a navigation element of a third type disposed on the navigation tracker, another registration between the robotic arm and the navigation tracker; and determine, based on the registration and the another registration, a first pose of the robotic arm relative to the anatomical element.

11. The system of claim 10, wherein the navigation element of the first type, the navigation element of the second type, and the navigation element of the third type are disposed on the navigation tracker in a predetermined configuration.

12. The system of claim 11, wherein the navigation element of the third type comprises an optical tracking target tracked by a third imaging device, and wherein determining the another registration comprises the processor:

receiving, from the third imaging device, first information about a first pose of the optical tracking target; and determining, based on the first information about the first pose of the optical tracking target and the predetermined configuration, a first position of the robotic arm relative to the navigation tracker.

13. The system of claim 12, wherein the navigation element of the first type includes a plurality of fluoroscopic markers capable of being detected by a fluoroscopic imaging device, and wherein the registration comprises the processor:

receiving, from the fluoroscopic imaging device, a plurality of images depicting the plurality of fluoroscopic markers and the anatomical element; and determining, based on the plurality of images, a position of each fluoroscopic marker of the plurality of fluoroscopic markers relative to the anatomical element.

14. The system of claim 13, wherein the navigation element of the second type includes a plurality of navigation markers capable of being detected by a second imaging device, and wherein the registration further comprises the processor:

receiving, from the second imaging device, information about a position of each navigation marker of the plurality of navigation markers; and determining, based on the information about the position of each navigation marker and the predetermined configuration, a position of each navigation marker relative to the anatomical element.

15. The system of claim 14, wherein the third imaging device is disposed proximate an end effector of the robotic arm.

16. The system of claim 15, wherein the robotic arm is disposed on a second table, the second table capable of moving relative to the patient bed.

17. The system of claim 15, wherein the second imaging device comprises a navigation camera, and wherein the third imaging device comprises a laser tracker.

18. A method, comprising:

determining, based on a first plurality of images captured by a first imaging device, a first registration between a plurality of fluoroscopic markers disposed on a navigation tracker and an anatomical element;

determining, based on a second plurality of image captured by a second imaging device, a second registration between a plurality of navigation markers disposed on the navigation tracker and the anatomical element;

determining, based on an optical sensor tracker target disposed on the navigation tracker, a third registration between the navigation tracker and a robotic arm; and moving, based on the second registration and the third registration, the robotic arm relative to the anatomical element.

19. The method of claim 18, wherein the plurality of fluoroscopic markers, the plurality of navigation markers, and the optical sensor tracker target are disposed in a fixed orientation on the navigation tracker.

20. The method of claim 19, wherein the optical sensor tracker target is tracked by a third imaging device, and wherein determining the third registration further comprises:

receiving, from the third imaging device, information describing a first location of the optical sensor tracker target relative to the robotic arm; and determining, based on the information describing the first location of the optical sensor tracker target, a first pose of the robotic arm relative to the navigation tracker.

* * * * *